(12) United States Patent
Wang et al.

(10) Patent No.: US 8,333,962 B2
(45) Date of Patent: Dec. 18, 2012

(54) CONTROLLED RELEASE MULTIDRUG FORMULATIONS FOR SPINAL CORD INJURY

(75) Inventors: Yu-Chao Wang, Taipei (TW); Yi-Ting Wu, Taoyuan (TW); Chung-Shi Yang, Taichung (TW)

(73) Assignee: National Health Research Institutes, Miaoli County (TW)

( * ) Notice: Subject to any disclaimer, the term of this patent is extended or adjusted under 35 U.S.C. 154(b) by 490 days.

(21) Appl. No.: 12/548,434

(22) Filed: Aug. 27, 2009

(65) Prior Publication Data

US 2011/0052711 A1   Mar. 3, 2011

(51) Int. Cl.
| | | |
|---|---|---|
| A61K 38/18 | (2006.01) |
| A61K 38/43 | (2006.01) |
| A61K 9/52 | (2006.01) |
| A61K 9/58 | (2006.01) |
| A61K 31/721 | (2006.01) |
| A61K 31/722 | (2006.01) |
| A61K 47/30 | (2006.01) |
| C07K 14/475 | (2006.01) |
| C07K 14/50 | (2006.01) |

(52) U.S. Cl. ............ 424/94.5; 424/94.2; 424/94.3; 424/423; 424/425; 424/426; 424/491; 424/501; 514/7.6; 514/8.3; 514/8.4; 514/8.9; 514/9.1; 514/17.2; 514/17.7; 514/21.2; 514/54; 514/55; 514/59; 514/772.3; 514/777

(58) Field of Classification Search .................. None
See application file for complete search history.

(56) References Cited

U.S. PATENT DOCUMENTS

| | | | |
|---|---|---|---|
| 2005/0287665 A1 | 12/2005 | Cheng et al. | |
| 2006/0177416 A1 | 8/2006 | Turnell et al. | |
| 2007/0116697 A1* | 5/2007 | Osterhout et al. | 424/94.61 |
| 2011/0244048 A1* | 10/2011 | Amiji et al. | 424/493 |
| 2011/0268807 A1* | 11/2011 | Su et al. | 424/491 |

OTHER PUBLICATIONS

Kimura et al., Regulatory Peptides, vol. 123, pp. 135-138, 2004.*
Jollivet et al., Biomaterials, vol. 25, pp. 933-942, 2004.*
Wang, Y. C.; Wu, Y. T.; Huang, H. Y.; Lo, L. W.; Tzeng, S. F.; Yang, C. S. (2008) Sustained intraspinal delivery of neurotrophic factor encapsulated in biodegradable nanoparticles following contusive spinal cord injury. Biomaterials 29:4546-4553.

* cited by examiner

*Primary Examiner* — Jeffrey Stucker
*Assistant Examiner* — Stephen Gucker
(74) *Attorney, Agent, or Firm* — Hsiu-Ming Saunders; Intellectual Property Connections, Inc.

(57) ABSTRACT

A controlled release multidrug formulation for improving locomotor recovery after spinal cord injury comprising: (a) a first composition comprising a first bioactive agent, encapsulated within a first polymeric particle; (b) a second composition comprising a second bioactive agent, encapsulated within a second polymeric particle, wherein the second polymeric particle is encapsulated within the first polymeric particle; and (c) a third composition comprising a third bioactive agent, encapsulated within either the first or the second polymeric particle, wherein the second composition is released subsequently to the release of the first composition, and wherein the first bioactive agent is a neurotrophic factor, the second bioactive agent is a collagen synthesis inhibitor, and the third bioactive agent is selected from the group consisting of cyclic AMP (cAMP), an adenylate cyclase activator and a Rho inhibitor.

18 Claims, 5 Drawing Sheets

FIG. 3A
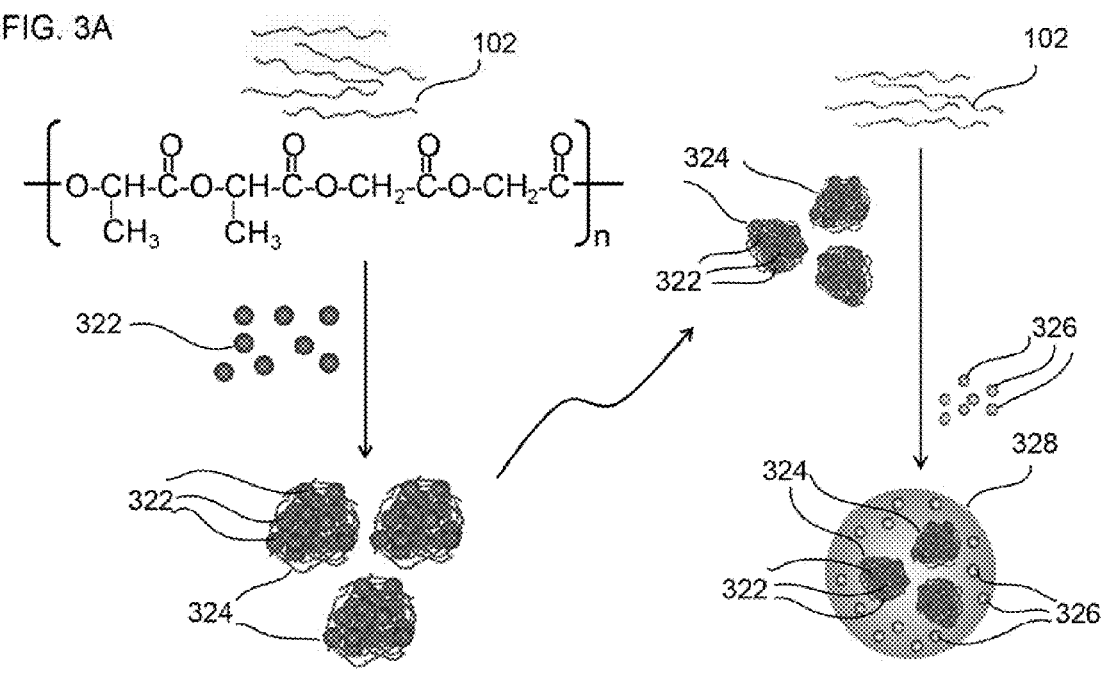
FIG. 3B
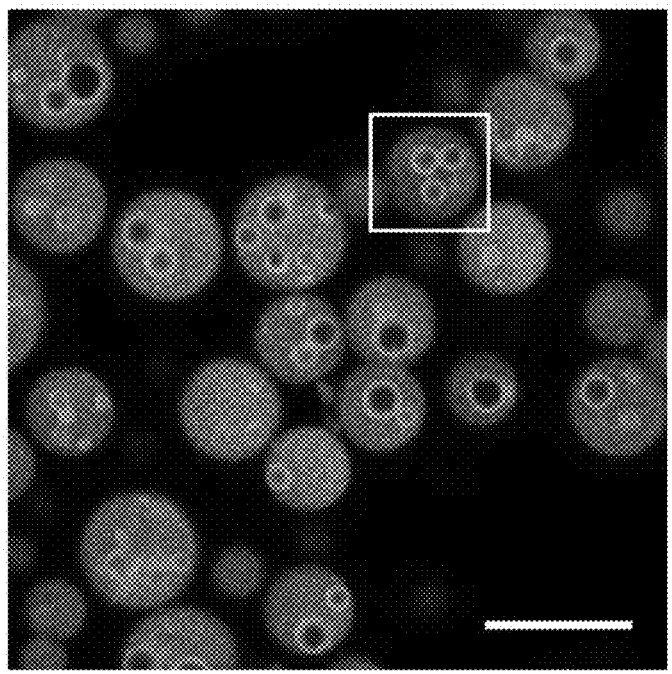
FIG. 3C
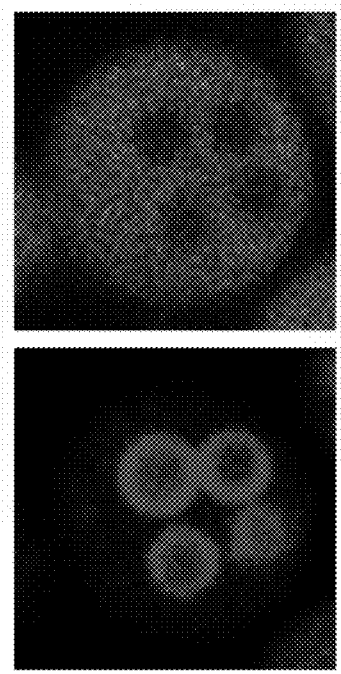
FIG. 3D

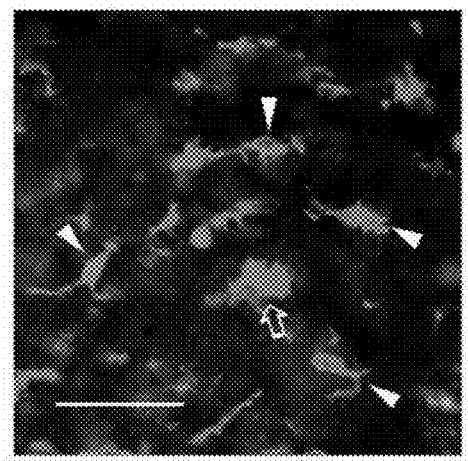
FIG. 5A
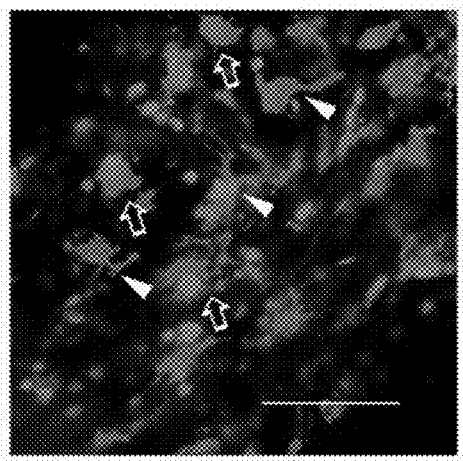
FIG. 5B
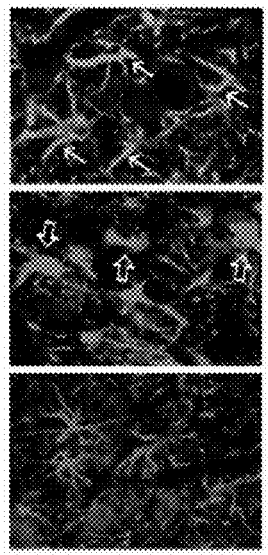
FIG. 5C
FIG. 5D
FIG. 5E
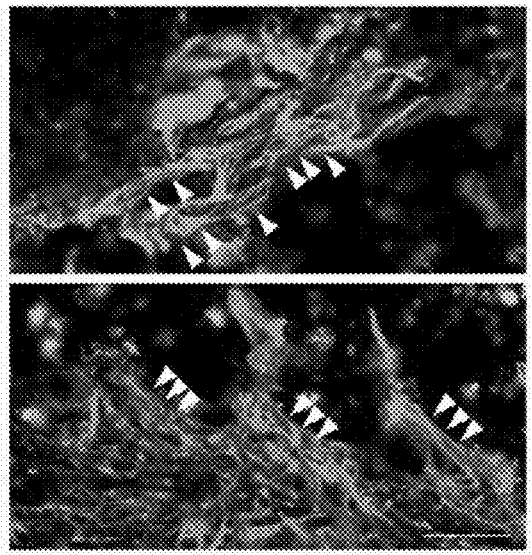
FIG. 5F
FIG. 5G

CONTROLLED RELEASE MULTIDRUG FORMULATIONS FOR SPINAL CORD INJURY

FIELD OF THE INVENTION

The present invention relates generally to a drug delivery system, and more specifically to a controlled release multidrug delivery system.

BACKGROUND OF THE INVENTION

Nearly 200,000 people in the U.S. live with a disability related to a spinal cord injury (SCI). SCI occurs when axons or nerve fibers of the spinal cord are interrupted, generally by mechanical forces. If the spinal cord is compressed, severed or contused, the axons may be physically or physiologically disintegrated so that no conduction of neuroelectric impulses can occur along the affected axon's length. Eventually, large populations of axons including their associated cell bodies may die, causing massive loss in communications between the brain and the peripheral nerves, and resulting in varying degrees of paraplegia or quadriplegia.

Typically, the treatment for SCI involves promoting neurological survival and axonal sprouting using neurotrophic and growth factors at the lesion site. Massive neural cell death occurring after SCI plays a critical role in the progress of secondary neurological damage. Thus, neuroprotective strategies to inhibit cell death and axonal dysfunction can decrease further functional loss after SCI. Among these strategies, application of neurotrophins and anti-inflammatory factors has shown promising effects on improving neuroprotection.

One problem that causes the failure of CNS neuron regeneration is inhibition of neurite outgrowth by certain bioactive molecules. Myelin contributes to a number of proteins that have shown to inhibit neurite process outgrowth. NogoA is the first protein identified on the surface of the oligodendrocytes and some axons. Other proteins that can contribute to inhibition include myelin-associated glycoprotein (MAG), oligodendrocyte-myelin glycoprotein (OMgp) and the proteoglycan versican.

The other source of major inhibitory activity lies with the formation of a glial scar after CNS injury. The scarring process involves a number of cells that can upregulate the synthesis and secretion of chondroitin sulfate proteoglycans (CSPG). CSPG accumulation occurs very rapidly at the lesion site, generally within one week post injury. It is believed that large glycosaminoglycan (GAG) sugar side chain within the CSPG are responsible for major inhibitory effects on axon elongation, by blocking access to growth promoting factors. It has also been demonstrated both in vitro and in vivo that axons can grow on a CSPG substrate if the GAG is removed by chondroitinase ABC (cABC) cleavage.

SCI presents an extreme set of problems to overcome to promote healing and reinnervation as many of the inhibitory molecules for the nerve regeneration appear at different stages post SCI. An effective treatment usually requires accommodating the dynamic changes in the microenvironment of the lesion site following SCI.

A previously unaddressed need exists in the art to address the deficiencies and inadequacies, especially in connection with provision of a formulation for releasing available therapeutic agents in a time-dependent sequential manner at the lesion site.

SUMMARY OF THE INVENTION

In one aspect, the invention relates to a controlled release multidrug formulation comprising: a) a first composition comprising a first bioactive agent, encapsulated within a first polymeric particle; b) a second composition comprising a second bioactive agent, encapsulated within a second polymeric particle, wherein the second polymeric particle is encapsulated within the first polymeric particle; and c) optionally a third composition comprising a third bioactive agent, encapsulated within either the first or the second polymeric particle, wherein the second composition is released subsequently to the release of the first composition.

In another aspect, the invention relates to a method for improving locomotor recovery after spinal cord injury (SCI) in a mammal comprising the step of intraspinal administration to the mammal of an effective amount of a controlled release multidrug formulation comprising: a) a first composition comprising a first bioactive agent, encapsulated within a first polymeric particle; b) a second composition comprising a second bioactive agent, encapsulated within a second polymeric particle, wherein the second polymeric particle is encapsulated within the first polymeric particle; and c) optionally a third composition comprising a third bioactive agent, encapsulated within either the first or the second polymeric particle, wherein the second composition is released subsequently to the release of the first composition, and wherein the first bioactive agent is a neurotrophic factor, the second bioactive agent is a collagen synthesis inhibitor, and the third bioactive agent is selected from the group consisting of cyclic AMP (cAMP), an adenylate cyclase activator and a Rho inhibitor, thereby improving locomotor recovery in the mammal.

In one embodiment of the invention, the first bioactive agent is a neurotrophic factor, the second bioactive agent chondroitinase ABC (ChABC), and the third bioactive agent is selected from the group consisting of cyclic AMP (cAMP), an adenylate cyclase activator and a Rho inhibitor.

In one embodiment of the invention, the neurotrophic factor is selected from the group consisting of GDNF, brain-derived neurotrophic factor (BDNF), basic fibroblast growth factor, nerve growth factor (NGF), neurotrophin 3 (NT3), neurotrophin 4 (NT4) and neurotrophin 5 (NT5). The adenylate cyclase activator is PACAP.

In another embodiment of the invention, the PACAP is encapsulated within the first polymeric particle.

In another embodiment of the invention, the Rho inhibitor is selected from the group consisting of C3-ADP-ribosyltransferase and BA-210 (Cethrin®).

In another embodiment of the invention, the first polymeric particle encapsulates more than one second polymeric particle encapsulating the second composition comprising the second bioactive agent.

In another embodiment of the invention, the first bioactive agent is glial cell-derived neurotrophic factor (GDNF), the second bioactive agent is chondroitinase ABC (ChABC), and the third bioactive agent is pituitary adenylate cyclase activating peptide (PACAP).

In another embodiment of the invention, the first polymeric particle comprises a hydrophobic polymer and the second polymeric particle comprises a hydrophobic or a hydrophilic polymer.

In another embodiment of the invention, the first polymeric particle comprises a hydrophilic polymer and the second polymeric particle comprises a hydrophobic or a hydrophilic polymer.

Further in another embodiment of the invention, the first polymeric particle comprises poly(lactic-co-glycolic acid) (PLGA), or chitosan and dextran sulfate.

Yet in another embodiment of the invention, the second polymeric particle comprises PLGA, or chitosan and dextran sulfate.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawins to refer to the same or like elements of an embodiment.

BRIEF DESCRIPTION OF THE DRAWINGS

FIG. 3A is a schematic drawing showing a process of making a controlled release multidrug formulation according to another embodiment of the invention.

FIGS. 3B-3D are confocal microscope images showing a controlled release multidrug formulation according to another embodiment of the invention. B: overlay of images C and D; C: image of 6-coumarin; D: image of phosphatidylethanolamine. Scale bar: 10 μm.

FIG. 5A is a photomicrograph of Iba1 staining of SCI spinal cord from a SCI rat treated with PLGA. Scale bar: 50 μm.

FIG. 5B is a photomicrograph of Iba1 staining of SCI spinal cord from a SCI rat treated with PLGA-GDNF. Scale bar: 50 μm.

FIG. 5C is a photomicrograph of GFAP staining of spinal cord from a SCI rat treated with PLGA. Scale bar: 50 μm.

FIG. 5D is a photomicrograph of GFAP staining of spinal cord from a SCI rat treated with PLGA-GDNF. Scale bar: 50 μm.

FIG. 5E is a photomicrograph of GFAP staining of spinal cord from a SCI rat treated with sham. Scale bar: 50 μm.

FIG. 5F is a photomicrograph of GFAP staining of spinal cord from a SCI rat treated with PLGA. Scale bar: 50 μm.

FIG. 5G is a photomicrograph of GFAP staining of spinal cord from a SCI rat treated with PLGA-GDNF. Scale bar: 50 μm.

DETAILED DESCRIPTION OF THE INVENTION

Definitions

Figure 1A:
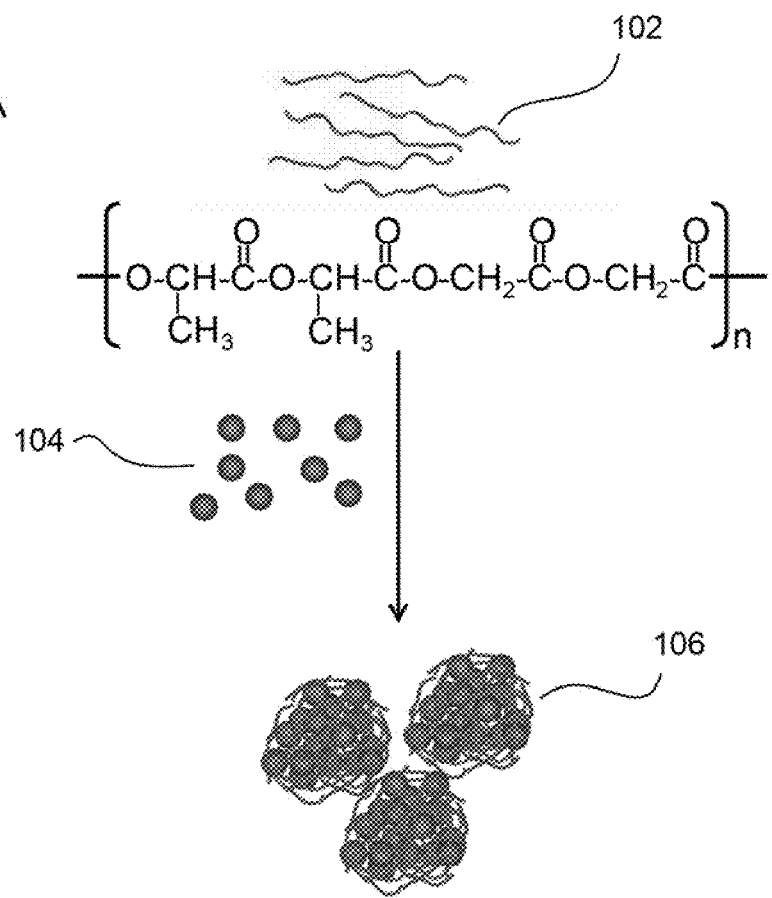
FIG. 1A is a schematic drawing showing a process of encapsulating a bioactive agent such as glial cell line-derived neurotrophic factor (GDNF) within PLGA particles.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "hydrophilic" means having a strong affinity for water.

As used herein, the term "hydrophobic" means repelling, tending not to combine with, or incapable of dissolving in water.

The full names for abbreviations used herein are as follows: "SCI" for spinal cord injury, "CS" for chitosan, "DS" for dextran sulfate, "GDNF" for glial cell line-derived neurotrophic factor, "ChABC" for chondroitinase ABC, "PLGA for poly(D,L-lactide-co-glycolide), "PVA" for poly(vinyl alcohol), "GFAP" for glial fibrillary acid proteins, "PE-Rh" for phosphatidylethanolamine (lissamine rhodamine B).

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Preparation of Bioactive Agent-Encapsulated Hydrophilic Particles

Chitosan (CS) and dextran sulfate (DS) were selected to form a hydrophilic nanoparticle core, which afforded a tighter physical structure than general CS nanoparticles. Chitosan (0.1% wt/vol) and dextran sulfate (0.1% wt/vol) solutions were prepared by dissolving CS in acetic acid and DS in ddH$_2$O, respectively. The concentration of acetic acid was kept 1.75 times higher than that of CS in all cases to maintain CS in the solution. To encapsulate a therapeutic agent such as chondroitinase ABC (ChABC) into a hydrophilic nanoparticle, 5 units of ChABC were dissolved in either the CS (1 ml) or DS (4 ml) solutions. The ChABC-entrapped nanoparticles were formed spontaneously upon addition of the CS (1 ml) solution to the DS (4 ml) solution with constant stirring for 15 minutes. The solution mixture was then subjected to an ultracentrifugation at 3000 rpm for 5 min to remove large aggregates and a further centrifugation at 40000 rpm for 30 min to collect the therapeutic agent-encapsulated CSDS nanoparticles. The therapeutic agent-encapsulated CSDS nanoparticles were washed twice with distilled, deionized water.

The CSDS nanoparticles were characterized for their mean particle diameter and size distribution by a 90 plus particle size analyser. While the average nanoparticle diameter was 260±100 nm, there was clearly a range of particle sizes generated with this manufacturing process. An analysis of the CSDS nanoparticles showed that most of the population has a diameter between 215-350 nm.

Other hydrophilic polymeric cores include, but not limited to, chitosan particles, gelatin particles, starch particles, agarose particles and hydrogel.

Example 2

Preparation of Bioactive Agent-Encapsulated Hydrophobic Particles

Poly(DL-lactide-co-glycolide) (PLGA), a hydrophobic polymer, was selected to form a hydrophobic particle shell. To encapsulate one or more than one therapeutic agent such as the growth factor GDNF and PACAP into a hydrophobic nanoparticle or particle, 50 µl of GDNF or GDNF plus PACAP water solution (2 µg/ml, dissolved in H$_2$O) was added drop-wise into 500 µl of PLGA (4 mg/ml, dissolved in the organic solvent dichloromethane without charge) solution. The mixed solution was sonicated under ice bath for 10 seconds to form the first emulsion (Water/Oil emulsion, i.e., H$_2$O/therapeutic agent molecules emulsified in the PLGA/organic solvent). The first emulsion solution (i.e., W/O) was immediately dropwisely added into 3 ml of sucrose solution (10% wt/vol in H$_2$O) or poly vinyl alcohol (PVA) solution (0.5% in H$_2$O) while vortexing. The mixed solution was sonicated under ice bath for 20 seconds to form the second emulsion (W/O/W, i.e., double emulsions: H$_2$O/therapeutic agent molecules emulsified in the PLGA/organic solvent emulsified in PVA or sucrose solution). The organic solvent was removed with a vacuum rotary evaporator to form hardened PLGA nanoparticles encapsulating one or more than one therapeutic agent (e.g., GDNF, or GDNF plus PACAP) in suspension, which were recovered by centrifugation.

FIG. 1A is a flow chart showing encapsulating rat GDNF 104 into PLGA particles 106. GDNF (R&D Systems)-encapsulated ALGA nanoparticles (PLGA-GDNF) were synthesized by a double emulsion solvent evaporation method. Twenty five microliters (25 µL) of GDNF 104 solution in citrate buffer (2 mg/mL, pH=8) was added drop-wise into 250 µL of PLGA 102 (PLA:PGA=50:50, MW 40,000-75,000, Sigma) solution in methyl chloride (2 mg/mL) and then sonicated with a microtip sonicator for 15 seconds on ice to create the first emulsion. The first emulsion was transferred into 1.5 mL of 10% sucrose solution and then sonicated for 20 seconds with the microtip sonicator (MICROSON XL2000, MISONIX) on ice to form the second emulsion. The organic solvent in the second emulsion was rapidly removed by using rotary evaporator (EYELA). Finally, the PLGA-GDNF particles 106 were concentrated by centrifugal ultrafiltration (Amicon Ultra, 10 kDa, Millipore) and stored at −80° C. until it was ready for use.

Other suitable hydrophobic polymeric materials that can be employed include, but not limited to, aliphatic polyesters, e.g., homopolymers or copolymers synthesized from one or more kinds of α-hydroxycarboxylic acids (e.g., glycolic acid, lactic acid, 2-hydroxybutyric acid, and valinic acid, leucic acid), hydroxydicarboxylic acids (e.g., malic acid), hydroxytricarboxylic acids (e.g., citric acid)), or their mixtures; poly-α-cyanoacrylic esters, e.g., poly(methyl α-cyanoacrylate), poly-(ethyl α-cyanoacrlate), poly(butyl α-cyanoacrylate); and amino acid polymers, e.g., poly(γ-benzyl-L-glutamate), or their mixtures. The mode of polymerization for these biodegradable polymers may be any of random, block or graft polymerization technique.

Example 3

Preparation of Hydrophilic Particle-Encapsulated Hydrophobic Particles

To form a drug delivery system comprising a hydrophilic nanoparticle embedded within a hydrophobic particle, a solution of hydrophilic nanoparticles encapsulating one or more than one therapeutic agent was mixed with at least another therapeutic agent before being added into another hydrophobic polymer solution. For example, 50 µl of ChABC-encapsulated CSDS nanoparticle solution was mixed with GDNF or GDNF/PACAP before being added into 500 µl of dichloromethane containing PLGA (10 mg/ml). The mixed solution was sonicated in an ice bath for 10 seconds to form the first emulsion (i.e., Water/Oil; ChABC-encapsulated CSDS nanoparticle and GDNF or GDNF/PACAP liquid suspended in PLGA liquid). The first emulsion solution was immediately added dropwisely into 3 ml (10% wt/vol) of sucrose solution or 0.5% PVA solution while vortexing. The mixed solution was sonicated in an ice bath for 20 seconds to form the second emulsion (i.e., Water/Oil/Water; ChABC-encapsulated CSDS nanoparticle and GDNF or GDNF/PACAP liquid suspended in PLGA liquid suspended in sucrose or PVA liquid). The organic solvent was removed with a vacuum rotary vapor and subjected to centrifugation to isolate particles each having a GDNF- or GDNF/PACAP-encapsulated PLGA shell surrounding ChABC-encapsulated CSDS nanoparticles.

The particles were characterized for their mean diameter and size distribution using a 90 plus particle size analyser. The particle sizes ranged from about 455 to about 625 nm with an average diameter of about 530±100 nm. Depending on the needs of the applications, the particle size for a drug delivery system according to the invention may be made in the range of micrometer size, e.g., from about 1 to 2 micrometers.

Figure 2A:
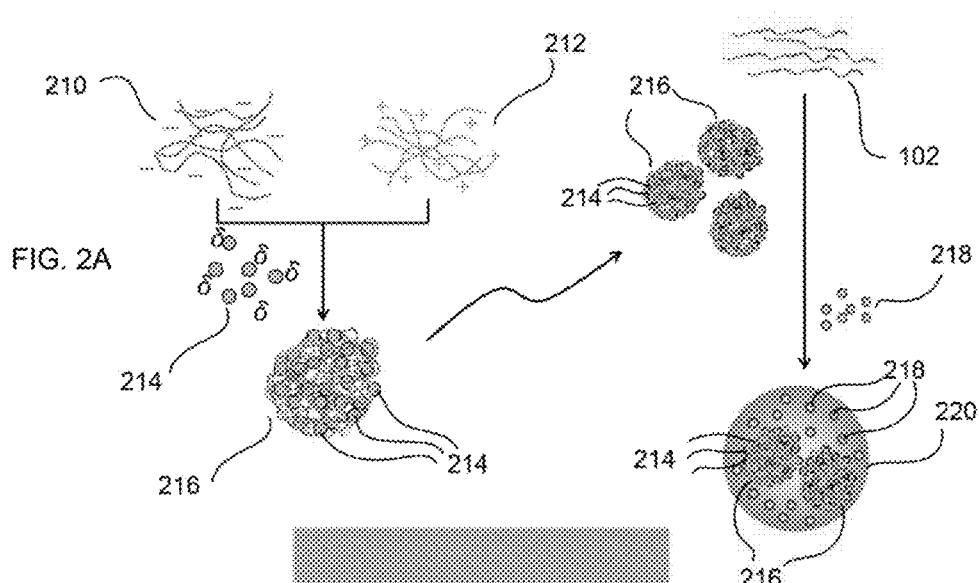
FIG. 2A is a schematic drawing showing a process of making a controlled release multidrug formulation according to one embodiment of the invention.

FIG. 2A illustrates a process of making hydrophilic nanoparticle-encapsulated hydrophobic microparticles 220. Dextran sulfate 210 and Chitosan 212 are added into a drug (such as protein drug) 214, which carries charges, to obtain a drug-encapsulated CSDS nanoparticle 216. The drug-encapsulated CSDS nanoparticles 216 are mixed with another bioactive agent 218 before addition of PLGA 102 to form CSDS-encapsulated ALGA microparticle 220, which encloses the drug-encapsulated CSDS 216 and another bioactive agent 218.

Figure 2B:
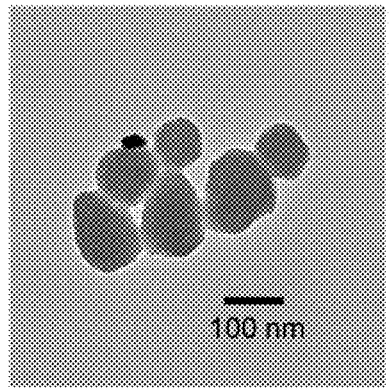
FIGS. 2B-2D are transmission electron microscope images. B: CSDS nanoparticles; C: CSDS nanoparticles-encapsulated PLGA particle (arrow); D: PLGA nanoparticles.
Figure 2C:
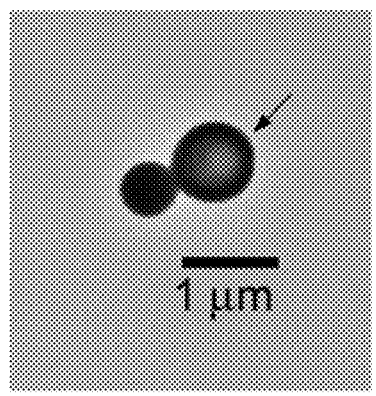
Figure 2D:
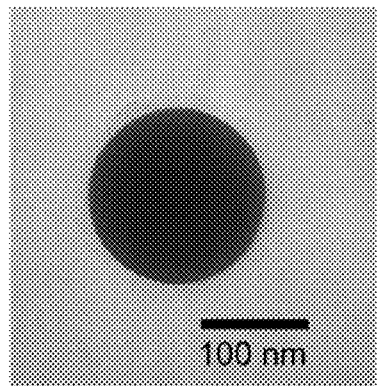

FIGS. 2B-2D are images of transmission electron microscope (TEM) taken with a Japan Hitachi, H-7650 instrument having an acceleration voltage of 80 kV, showing CSDS nanoparticles (FIG. 2B), CSDS nanoparticle encapsulated within a PLGA particle (FIG. 2C) and a PLGA particle without encapsulating a CSDS nanoparticle (FIG. 2D). Under the TEM, a PLGA particle comprising an inner CSDS particle displayed an internal white image as shown in FIG. 2C (arrow). The PLGA particle without enclosing a CSDS particle displayed a dark image as shown in FIG. 2D.

Example 4

Preparation of Hydrophobic Particle-Encapsulated Hydrophobic Particles

To form a drug delivery system containing a hydrophobic nanoparticle embedded within a hydrophobic particle, a solution of hydrophobic polymeric nanoparticles encapsulating one or more than one therapeutic agent was mixed with at least another therapeutic agent before being added into another hydrophobic polymer solution. For example, 50 µl of ChABC-encapsulated PLGA nanoparticle solution was mixed with GDNF or GDNF/PACAP before being added into 500 µl of dichloromethane containing PLGA (10 mg/ml). The mixed solution was sonicated in an ice bath for 10 seconds to form the first emulsion (i.e., Water/Oil; ChABC-encapsulated PLGA nanoparticle and GDNF or GDNF/PACAP liquid suspended in PLGA liquid). The first emulsion solution was immediately added dropwisely into 3 ml (10% wt/vol) of sucrose solution or 0.5% PVA solution while vortexing. The mixed solution was sonicated in an ice bath for 20 seconds to form the second emulsion (i.e., Water/Oil/Water; ChABC-encapsulated PLGA nanoparticle and GDNF or GDNF/PACAP liquid suspended in PLGA liquid suspended in sucrose or PVA liquid). The organic solvent was removed with a vacuum rotary vapor and subjected to centrifugation to isolate particles each having a GDNF- or GDNF/PACAP-encapsulated PLGA shell surrounding ChABC-encapsulated PLGA nanoparticles.

FIG. 3A illustrates a process of making a hydrophobic nanoparticle-encapsulated within a hydrophobic microparticle 328, in which the inner hydrophobic nanoparticle 324 encloses a first bioactive agent 322 and the outer microparticle 328 further encloses a second bioactive agent 326. To make the inner hydrophobic nanoparticle 324 enclosing the first bioactive agent 322, PLGA 102 is added into the first bioactive agent 322. The PLGA 102 forms a hydrophobic particle 324 encapsulating the first bioactive agent 322. To make the outer microparticle 328 enclosing the inner hydrophobic nanoparticle 324 and a second bioactive agent 326, PLGA 102 is added into a mixture of the inner hydrophobic nanoparticle 324, which encloses the first bioactive agent 322, and a second bioactive agent 326. The PLGA 102 forms a microparticle 328 that encloses both the first bioactive agent 322 the second bioactive agent 326, in which the first bioactive agent 322 is encapsulated within the hydrophobic nanoparticle 324 and the second bioactive agent 326 is encapsulated within the outer hydrophobic microparticle 328.

The particles were characterized for their mean particle diameter. The particle sizes ranged from about 0.5 to about 10 µm with an average diameter of about 5 µm. Depending on the needs of the applications, the particle size for a drug delivery system according to the invention may be made in the range of micrometer size such as from about 1 to 2 µm.

Example 5

Multiphasic Drug Encapsulation

Two hundred microliters of PLGA (100 mg/ml, dissolved in the organic solvent dichloromethane) and PE-Rh (phosphatidylethanolamine (lissamine rhodamine B)) (5 µg/ml, dissolved in the organic solvent dichloromethane) solution was added drop-wise into 2 ml of poly vinyl alcohol (PVA) solution (0.5% in H2O) while vortexing. The mixed solution was sonicated under an ice bath for 30 seconds to form a single emulsion (Oil/Water, i.e., PLGA and PE-Rh/organic solvent emulsified in PVA solution). The organic solvent was removed with a vacuum rotary evaporator to form hardened PE-Rh-encapsulated PLGA nanoparticles in suspension, which were recovered by centrifugation.

Fifty microliters of PE-Rh-encapsulated PLGA nanoparticle solution was added into 500 µl of dichloromethane containing PLGA (10 mg/ml) and 6-coumarin (5 µg/ml). The mixed solution was sonicated in an ice bath for 30 seconds to form the first emulsion (i.e., Water/Oil; PE-Rh-encapsulated PLGA nanoparticle liquid suspended in PLGA/6-coumarin liquid). The first emulsion solution was immediately added dropwisely into 3 ml (0.5% wt/vol) of PVA solution while vortexing. The mixed solution was sonicated in an ice bath for 30 seconds to form a second emulsion (i.e., Water/Oil/Water; PE-Rh-encapsulated PLGA nanoparticle liquid suspended in PLGA/6-coumarin liquid suspended in PVA liquid). The organic solvent was removed with a vacuum rotary vapor and subjected to centrifugation to isolate particles each having a 6-coumarin-encapsulated PLGA shell surrounding a PE-Rh-encapsulated PLGA core nanoparticles.

The red fluorescence of PE-Rh was observed by confocal (SPE, Leica) at emission wavelength of 580 nm excited by 532 nm laser, whereas the green fluorescence of 6-coumarin was observed at emission wavelength of 510 nm excited by 488 nm laser.

FIGS. 3B-3D shows PLGA microparticles that enclose two bioactive agents, 6-coumarin and PE-Rh, in which the agent PE-Rh but not the agent 6-coumarin was encapsulated within a PLGA nanoparticle. The agent 6-coumarin makes green fluorescence and the agent PE-Rh makes red fluorescence. The boxed area in FIG. 3B is shown magnified in FIGS. 3C and 3D. The image in FIG. 3C was taken with excitation and emission filters for green fluorescence, the image in FIG. 3D taken with filters for red fluorescence and the image in FIG. 3B an overlay of images FIGS. 3C and 3D. As shown in FIG. 3B, the two fluorescent dyes were completely segregated with the red dye in discrete particles and green dye distributed outside the red particles but enclosed within a microparticle. When the boxed area image was taken for green fluorescence, a distribution of green fluorochrome molecules within the microparticle was observed except four discrete spots (FIG. 3C). When its image was taken for red fluorescence, four discrete red particles were observed within the microparticle (FIG. 3D).

Example 6

In Vitro Release and Stability

PLGA-GDNF

The in vitro release of GDNF from PLGA particles was evaluated in Neurobasal medium (Life Technologies) at 37°

C. In 96-well titer plate, 100 μg of PLGA-GDNF nanoparticles were suspended in 20 mL medium and the solution was dispensed into each well. At predetermined times, 80 μL were collected from the well and the concentration was determined by a GDNF ELISA kit (R&D Systems).

PLGA-BSA

A known quantity of BSA-encapsulated nanoparticle suspension was centrifuged at 15000 rpm for 30 minutes at 4° C. The supernatant solution was decanted and the collected BSA-encapsulated nanoparticles were then resuspended and incubated in 5 ml of 10 mM phosphate buffer (pH 7.4), 100 mM phosphate buffer (pH 7.4), or water, each with controlled agitation at 37° C. The quantity of BSA-encapsulated nanoparticles was adjusted to obtain a BSA concentration of 1 mg/ml per release study. At designated time intervals, samples were centrifuged at 15000 rpm and 5 ml of the supernatant was removed and replaced by an equal volume of fresh medium. The amount of BSA released at various time intervals was determined using the Bradford protein assay method. BSA calibration curves were made with fresh BSA dissolved in the incubation medium. All measurements were performed in triplicate. The empty, non-encapsulated CSDS nanoparticles were incubated at 37° C. and analyzed by the same method to act as a control.

The stability of BSA-encapsulated nanoparticles was examined by evaluating the integrity of the released BSA by SDS-PAGE analysis. The released samples were lyophilized to concentrate the protein before being used for SDS-PAGE. The lyophilized released sample was dissolved in 50 μL of Tris-glycine SDS-PAGE sample buffer containing 0.1% bromophenol blue and 20% glycerol. The dissolved sample solutions as well as molecular standards (6.6-200 kDa) were loaded to Tris-glycine gradient gel (8%-16%). The released medium collected from empty, non-encapsulated CSDS nanoparticles was treated in the same fashion and used as a control. Gel electrophoresis was performed using a Mini-Protein II cell (Bio-Rad Laboratories) at a constant voltage (150V) for 90 minutes using Power PAC 300 (Bio-Rad Laboratories) with a running buffer containing 25 mM Tris, 192 mM glycine, and 0.1% SDS at pH 8.3. The sample bands were stained for 30 minutes with 0.1% Coomassie blue R-250 solution containing 10% acetic acid and 25% isopropanol, followed by destaining overnight with a solution of 50% acetic acid in isopropanol. The separation of BSA on the gel was visualized using a gel image system (Kodak Digital Science1D, Rochester, N.Y.).

Example 7

Treatment of Spinal Injury

Methods

Figure 4A:
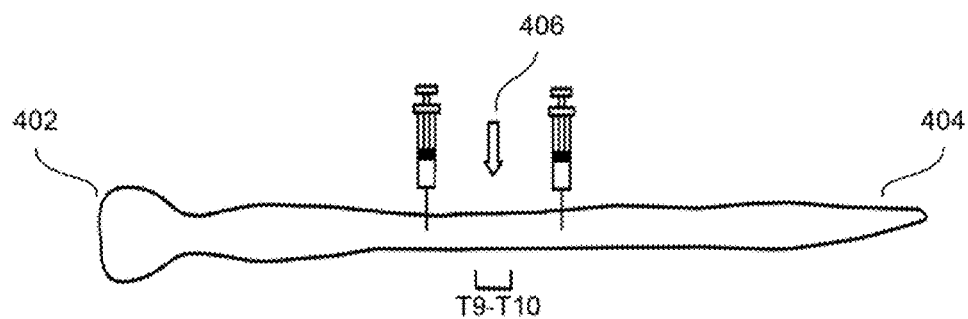
FIG. 4A is a diagram showing the position of PLGA-GDNF injection after spinal cord contusion.

Spinal cord contusion and Injection of hydrophobic particles encapsulating a therapeutic agent. Spinal cord axonal injury was induced experimentally on rats according to the procedures as described previously (Yang et al., (2008) "Sustained intraspinal delivery of neurotrophic factor encapsulated in biodegradable nanoparticles following contusive spinal cord injury" Biomaterials 29, 4546-4553, which is incorporated herein by reference in its entirety). Briefly, female adult SD rats (250 g±30) were anesthetized, and their spinal cords were exposed by laminectomy at the level of T9/T10 (FIG. 4A). A 10-g rod was dropped onto the laminectomized cord from a height of 25 mm (moderate SCI) and 50 mm (severe SCI) using a device developed at the New York University. During surgery the rectal temperature was maintained at 37° C. with a heating pad controlled by a thermostat.

The injection of nanoparticles was performed immediately after SCI. A 5-μL Exmire micro-syringe with a 31-gauge needle attached was positioned at the midline of the L1 level and stereotaxically inserted 0.7-0.8 mm below the dura. PLGA-GDNF (2 μg/5 μL/injection; 4 μg/rat; n=6), or PLGA (5 μL/injection; 10 μL/rat; n=6) nanoparticles were injected into approximately 1-2 mm rostral 402 and caudal 404 to the lesion epicenter 406 (FIG. 4A). After each injection, the needle was maintained in the spinal cord for an additional 2 min to reduce the possibility of the leakage of the injected fluid from the site. Animals were then housed in pairs, and manually bladder evacuation was performed at least twice a day. In addition, the injured animals received antibiotics (sodium ampicillin, 80 mg/kg/day) daily for a week after SCI. Animal care was provided in accordance with the *Laboratory Animal Welfare Act, Guide for the care and Use of Laboratory Animals* approved by Institutional Animal Care and Use Committee of National Cheng Kung University.

Evaluation of hindlimb locomotor function. The motor function of animals which had received either PLGA or PLGA-GDNF was assessed weekly by two blinded observers, using BBB hindlimb locomotor rating scale. Locomotor activities were evaluated by placing animals for 4 min in the open-field with a molded plastic surface. Hindlimb locomotor recovery in animals was scored on the scale of 0 (no hindlimb movement) to 21 (normal mobility).

Tissue preparation and immunofluorescence. Experimental animals were perfused intracardially with 0.9% cold NaCl (400 ml/rat on average), followed by 4% paraformaldehyde in 0.1 M phosphate buffer (500 ml/rat). Spinal cord tissues were removed, post-fixed in 4% paraformaldehyde overnight, and then cryoprotected in 30% (w/v) sucrose in PBS for 1 day. Approximately 2 cm of the spinal cords, including the epicenter, were embedded in Tissue Tek OCT (Miles), and cut longitudinally in 20 μm sections. The tissues were rinsed in PBS three times and stained with Nuclear Red or DAPI.

Tissue sections were rinsed three times with PBS and incubated for 30 min with 0.1% Triton X-100 in PBS containing 5% normal goat serum to increase the permeability and reduce nonspecific binding. Primary rabbit antibodies, anti-neurofilament-200 kDa (NF; Sigma), a marker for neurons, anti-Iba1 (Wako), a marker for microglia and anti-GFAP (Chemicon), a marker for neuroglia, were diluted 1:200 and incubated with the sections overnight at 4° C. in a humidified chamber. After rinsing with PBS, the sections were incubated at room temperature with biotinylated secondary antibodies for 1 h, rinsed, and incubated with fluorescein-avidin for 45 min at room temperature. The immunolabeled sections were post-stained with DAPI to show cellular nuclei. Images were captured using a Nikon E-800 microscope equipped with a cooled CCD system.

Results

Figure 1B:
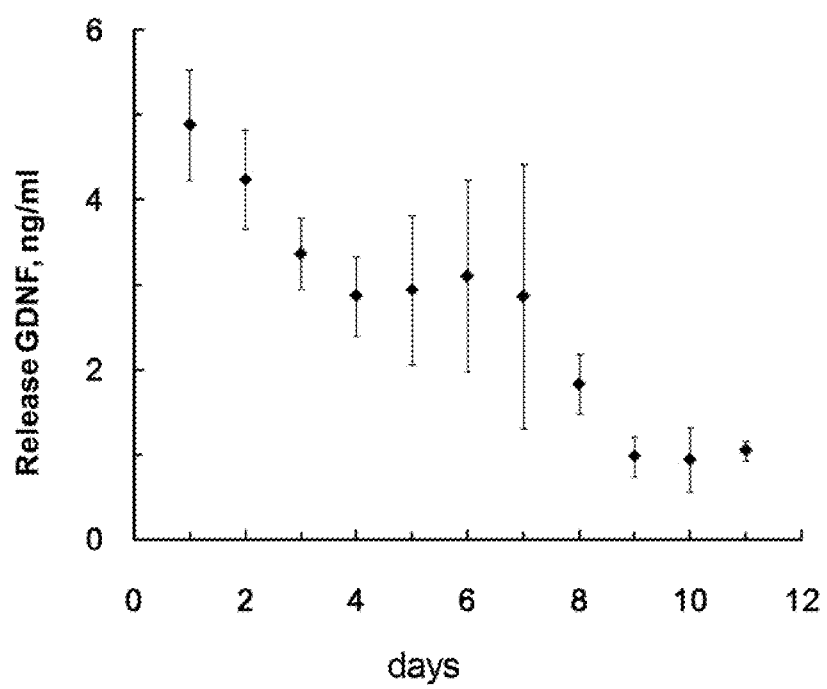
FIG. 1B is a graph showing release of encapsulated GDNF from PLGA particles over time.
Figure 4B:
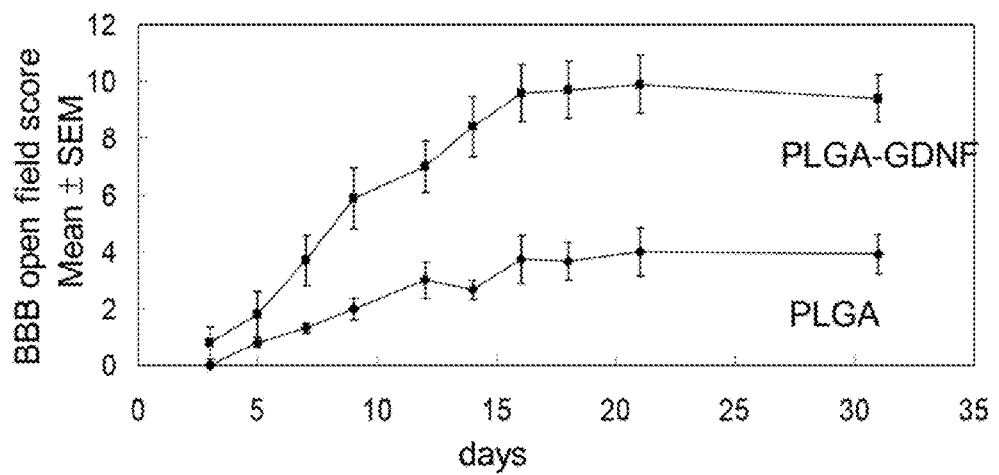
FIG. 4B is a graph of the motor score of SCI rats treated with PLGA and PLGA-GDNF over time.
Figures 4C, 4D:
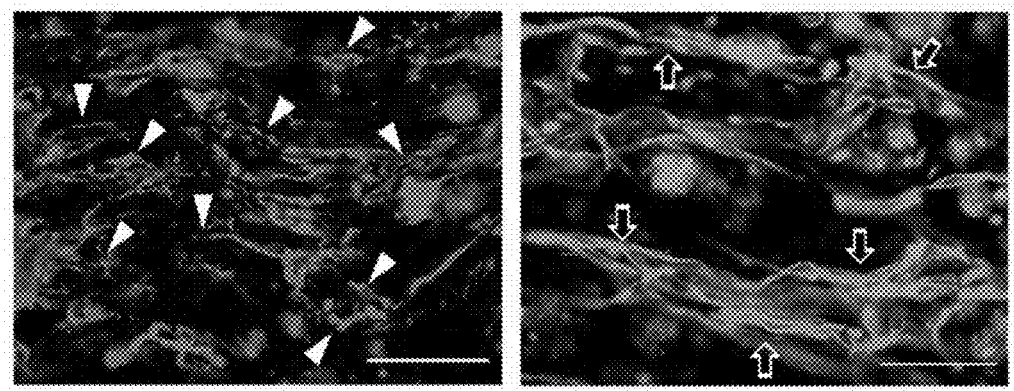
FIG. 4C is a photomicrograph of neurofilament staining of spinal cord from SCI rats treated with PLGA. Scale bar: 50 μm.
FIG. 4D is a photomicrograph of neurofilament staining of spinal cord from a SCI rat treated with PLGA-GDNF. Scale bar: 50 μm.

The in vitro release profile of GDNF from PLGA nanoparticles indicated a sustained release over seven days of the experiment (FIG. 1B). The effects on motor function of dual spinal cord injection of PLGA and PLGA-GDNF into the injured spinal cord right after severe SCI are shown in FIG. 4B. The hindlimb locomotor function was assessed every 2-3 days up to 31 days using the BBB locomotor rating scale. The PLGA-treated rats showed only a slight movement in their motor score. Their scores improved to only 1.3±0.2 in the first week, 2.7±0.3 in the second week, and only 3.9 by the end of 31 days. In contrast, the scores of the PLGA-GDNF treated rats increased much more. The PLGA-GDNF treaded rat scores improved to 3.7±0.9 in one week, 8.4±1.1 in two weeks, and 9.5±0.8 in 31 days. This is much more than has been previously seen with GDNF treatment and corresponds to weight-supported plantar steps Immunofluorescence showed that there were elongated intact neuronal fiber bundles with neurofilament-positive staining in the lesion center of the spinal cord from a SCI rat receiving PLGA-GDNF treatment (FIG. 4D, arrows), whereas only numerous fine fragmented neuronal fibers remained in the lesion center of the spinal cord from a PLGA-treated SCI rat (FIG. 4C, arrowheads). The results indicate that treatment with the PLGA-GDNF exerted effective neuroprotection on spinal neurons, an important factor in hindlimb locomotion recovery in rats with severe SCI. In contrast, the morphological examination showed that multiple types of Iba1-stained microglia scattered through the lesion center of the spinal cord were observed in both PLGA-treated and PLGA-GDNF-treated SCI rat spinal cords (FIGS. 5A and 5B, arrows indicating amoeboid-shaped Iba1$^+$ microglia and arrowheads indicating ramified Iba1$^+$ microglia). In addition, the accumulation of astrocytes with GFAP immunoreactivity along the periphery of the cavity was observed (FIGS. 5F and 5G, arrowheads). In comparison with that observed in sham (i.e., uninjured) spinal cord (FIG. 5E), a clear hypertrophic shape of astrocytes was also found in the injured spinal cord treated with either PLGA or PLGA-GDNF (FIGS. 5C and 5D, arrows). The findings suggest that intraspinal administration of PLGA-GDNF into the injured spinal cord had no influence on glial activation.

This study shows that GDNF encapsulated in ALGA nanoparticles was effective in the experimental treatment of animals with severe SCI. It was demonstrate that GDNF loaded in PLGA could be continually released. When injected near the site of SCI, PLGA-GDNF caused an improvement in neuronal survival and greater restoration of motor function.

The invention relates to a controlled release multidrug formulation for improving locomotor recovery after spinal cord injury. The formulation comprises: (a) a first composition comprising a first bioactive agent, encapsulated within a first polymeric particle; (b) a second composition comprising a second bioactive agent, encapsulated within a second polymeric particle, wherein the second polymeric particle is encapsulated within the first polymeric particle; and (c) a third composition comprising a third bioactive agent, encapsulated within either the first or the second polymeric particle. The second composition is released subsequently to the release of the first composition, and the first bioactive agent is a neurotrophic factor, the second bioactive agent is a collagen synthesis inhibitor, and the third bioactive agent is selected from the group consisting of cyclic AMP (cAMP), an adenylate cyclase activator and a Rho inhibitor (Thuret et al., (2006) "Therapeutic interventions after spinal cord injury" Nature Reviews, Neuroscience Vol 7: 628-643, which is herein incorporated by reference in its entirety).

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A controlled release multidrug formulation comprising:
    a) a first composition comprising glial-derived neurotrophic factor (GDNF) or brain-derived neurotrophic factor (BDNF), encapsulated within a first polymeric particle;
    b) a second composition comprising chondroitinase ABC (ChABC), encapsulated within a second polymeric particle, wherein the second polymeric particle is encapsulated within the first polymeric particle; and
    c) optionally a third composition comprising a bioactive agent selected from the group consisting of cyclic AMP (cAMP), an adenylate cyclase activator and a Rho inhibitor, the third composition being encapsulated within either the first or the second polymeric particle, wherein chondroitinase ABC (ChABC) of the second composition is released subsequently to the release of the first composition.

2. The formulation of claim 1, wherein the neurotrophic factor is glial cell-derived neurotrophic factor (GDNF).

3. The formulation of claim 1, wherein the adenylate cyclase activator is pituitary adenylate cyclase activating peptide (PACAP).

4. The formulation of claim 3, wherein the PACAP is encapsulated within the first polymeric particle.

5. The formulation of claim 1, wherein the Rho inhibitor is selected from the group consisting of C3-ADP-ribosyltransferase and BA-210.

6. The formulation of claim 1, wherein the first polymeric particle comprises poly(lactic-co-glycolic acid) (PLGA) and the second polymeric particle comprises PLGA, or chitosan and dextran sulfate.

7. The formulation of claim 1, wherein the first polymeric particle comprises PLGA, or chitosan and dextran sulfate.

8. The formulation of claim 1, wherein the neurotrophic factor is glial cell-derived neurotrophic factor (GDNF), and the third bioactive agent is pituitary adenylate cyclase activating peptide (PACAP).

9. A method for improving locomotor recovery after spinal cord injury (SCI) in a mammal comprising:
    intraspinal administration to the mammal an effective amount of a controlled release multidrug formulation of claim 1, and thereby improving locomotor recovery in the mammal.

10. The method of claim 9, wherein the neurotrophic factor is glial cell-derived neurotrophic factor (GDNF), and the third bioactive agent is pituitary adenylate cyclase activating peptide (PACAP).

11. The method of claim 9, wherein the first polymeric particle comprises poly(lactic-co-glycolic acid) (PLGA), or chitosan and dextran sulfate.

12. The method of claim 9, wherein the second polymeric particle comprises PLGA, or chitosan and dextran sulfate.

13. The method of claim 9, wherein the first polymeric particle comprises a hydrophobic polymer and the second polymeric particle comprises a hydrophobic or a hydrophilic polymer.

14. The method of claim 9, wherein the first polymeric particle comprises a hydrophilic polymer and the second polymeric particle comprises a hydrophobic or a hydrophilic polymer.

15. A controlled release multidrug formulation comprising:
   a) a first composition comprising glial cell-derived neurotrophic factor (GDNF) encapsulated within a first polymeric particle; and
   b) a second composition comprising chondroitinase ABC (ChABC), encapsulated within the second polymeric particle,
   wherein the second polymeric particle is encapsulated within the first polymeric particle; and
   further wherein the second composition is released subsequently to the release of the first composition.

16. The formulation of claim 15, further comprising a third composition, the third composition comprising a third bioactive agent, encapsulated within either the first or the second polymeric particle.

17. A method for improving locomotor recovery after spinal cord injury (SCI) in a mammal comprising:
   intraspinal administration to the mammal an effective amount of the controlled release multidrug formulation of claim 15, and thereby improving locomotor recovery in the mammal.

18. A method for improving locomotor recover after spinal cord injury (SCI) in a mammal comprising:
   intraspinal administration to the mammal an effective amount of the controlled release multidrug formulation of claim 16, and thereby improving locomotor recovery in the mammal.

\* \* \* \* \*